United States Patent [19]

Hirai et al.

[11] Patent Number: 5,216,127
[45] Date of Patent: Jun. 1, 1993

[54] ADSORBENT FOR SERUM AMYLOID PROTEIN

[75] Inventors: Fumiyasu Hirai, Amagasaki; Nobutaka Tani, Osaka, both of Japan

[73] Assignee: Kanegafuchi Kagaku Kogyo Kabushiki Kaisha, Osaka, Japan

[21] Appl. No.: 729,234

[22] Filed: Jul. 12, 1991

Related U.S. Application Data

[63] Continuation of Ser. No. 272,960, Nov. 18, 1988, abandoned.

[30] Foreign Application Priority Data

Nov. 20, 1987 [JP] Japan ................. 62-294810
Nov. 20, 1987 [JP] Japan ................. 62-294811
Dec. 25, 1987 [JP] Japan ................. 62-330617

[51] Int. Cl.$^5$ .......... A61K 35/14; A61K 31/185; A61K 31/205; A23J 1/00
[52] U.S. Cl. .................. 530/380; 530/386; 530/415; 514/553; 514/554; 514/647; 514/649; 514/679
[58] Field of Search ........... 530/380, 415, 47, 386; 514/649, 647, 579, 553, 554

[56] References Cited

U.S. PATENT DOCUMENTS 4,100,149  7/1978  Meiller ..................... 530/380
4,782,014  11/1988  Serban ..................... 530/386

FOREIGN PATENT DOCUMENTS 0206302  12/1986  European Pat. Off. .

OTHER PUBLICATIONS

Pepys et al, 105 Clin. Chem. ACTA 83-82 (1980) (Abstract).
Ku et al, 158 J. Exp. Med. 767-780 (1983) (Abstract).
Kato et al, 31 Jikeikai Med. J. 165-167 (Abstract).
Parker et al, 9 Biochem. 1074-1082 (1970).
Ortega et al, Chemical Abstracts 102:44057c (1985).

Primary Examiner—John W. Rollins
Attorney, Agent, or Firm—Armstrong, Westerman, Hattori, McLeland & Naughton

[57] ABSTRACT

An adsorbent for a serum amyloid protein, which includes a water-insoluble carrier and either a compound selected from a compound having an anionic functional group, a polyanionic compound having more than one anionic functional groups, aniline and an aniline derivative, the compound being immobilized onto the carrier, or a group of the formula: —NR$^1$R$^2$, wherein R$^1$ is hydrogen atom, methyl group or ethyl group, and R$^2$ is an atomic group satisfying that the value of log P, in which P is a distribution coefficient in a water-octanol system, of a compound of the formula: R$^2$H is from 0 to 3.2, the group being bonded to the carrier, and a method for removing a serum amyloid protein from body fluid through a removing apparatus using the above adsorbent. According to the present invention, SA proteins, particularly SAA proteins and SAP proteins can be selectively removed from body fluid without decreasing HDL largely. Besides, the adsorbent can be provided at a low cost.

8 Claims, 1 Drawing Sheet

FIG. 1

ADSORBENT FOR SERUM AMYLOID PROTEIN

This is a continuation of application Ser. No. 07/272,960 filed Nov. 18, 1988 now abandoned.

BACKGROUND OF THE INVENTION

The present invention relates to an adsorbent for serum amyloid (hereinafter referred to as "SA") protein from body fluid. Particularly, the present invention relates to an adsorbent for serum amyloid A (hereinafter referred to as "SAA") protein and serum amyloid P (hereinafter referred to as "SAP") protein from body fluid.

There is a disease called amyloidosis attended with serious troubles, for example, insufficiency of organs such as heart and kidney, disturbance of impulse conducting system, progressive dementia, cerebrovascular disease, nerve trouble and so on. Amyloidosis is caused by a deposition of β-fibril-like amyloid on a blood vessel, a certain organ and so on. It is known that there are some types of amyloidosis, i.e. primary amyloidosis, secondary amyloidosis, familial amyloidosis, senile amyloidosis, and so on, and that the composition of proteins causing amyloidosis differs depending on the type of amyloidosis.

Secondary amyloidosis follows diseases such as rheumatoid arthritis, juvenile rheumatoid arthritis, suppurative diseases of the lung and pulmonary tuberculosis. There are exemplified as favourite localization in secondary amyloidosis, kidney, thyroid gland, pancreas, liver, spleen and the like.

In secondary amyloidosis, deposited amyloids are formed from amyloid A (hereinafter referred to as "AA") protein which is a protein having a molecular weight of 8,500 and composing of 76 amino acids.

It becomes clear step by step that there exist a precursor, in patient's body fluid, corresponding to each deposited amyloid in each type of amyloidosis.

It is considered that SAA protein which is one of apolipoproteins of high density lipoproteins (hereinafter referred to as "HDL") is the precursor corresponding to AA protein being the deposited amyloid of the secondary amyloidosis. SAA protein has a molecular weight of about 12,000, and it is thought that the protein is produced in hepatic cell, forms apolipoprotein of HDL in blood, circulates through the body and separated from HDL to be hydrolyzed to form AA protein, and then, the AA protein is deposited in tissues. Also, it is thought that SAA protein exists as an apolipoprotein of $HDL_3$ which has a high density compared with other HDL, and has a molecular weight of $1.75 \times 10^5$.

In the 1960's, it was proved that there are two kinds of amyloids by means of investigation with electron microscope. That is, one is an amyloid having a shape of fiber peculiar to amyloids (amyloid fibrils), and the other is a pentagonal rod-like amyloid (P-component, AP).

In every type of amyloidosis except in macula of cerebrum in Alzheimer's disease or presbyophrenia senile dementia, a substance called amyloid P (hereinafter referred to as "AP") protein can be found in the state of combining with a β-fibril-like protein.

As to the structure of AP protein, it is reported that the unit is formed as a pentagon by five subunits, the subunit having a molecular weight of 23,000 to 25,000, and the structure of AP protein is constructed by a pair of the unit making a parallel form.

It is confirmed that the AP protein is the same as SAP protein which is a normal serum protein by means of various methods. Accordingly, it is considered that AP protein is SAP protein deposited in tissue during circulation, that is, SAP protein is a precursor corresponding to AP protein. Although the function of AP protein in body and the relation of the protein with other amyloids are not clarified completely. However, there is a report that AP protein is an indispensable protein for an amyloid fibril. Accordingly, it is thought that the deposition of SAP protein is involved in the onset of amyloidosis.

Therapy for amyloidosis has been eagerly studied since, as described above, amyloidosis is a serious disease and its mortality is high. However, effective therapy especially drug therapy has not been found.

On the other hand, there has been tried a blood purification by extracorporeal circulation treatment, particularly plasmapheresis for treatment of amyloidosis, and there are some reports that symptom decreases and lesion progress is stopped by exchange blood plasma containing the above mentioned precursors in a large amount with normal plasma.

Blood purification particularly plasmapheresis is the most effective therapy at present. However, the above blood purification has defects that it requires expensive and precious normal plasma or plasma preparations, that, in carrying out blood purification, useful components other than the precursors contained in a patient's plasma are removed at the same time, and the like. Therefore there is strongly desired a development of method for more selectively removing precursors such as SAA protein and SAP protein.

An object of the present invention is to solve the above problems and to provide a low-cost adsorbent for SA proteins, which can selectively remove SA proteins. Particularly, the object is to provide a low-cost SAA protein adsorbent which can selectively remove SAA proteins without removing HDL, and a low-cost SAP protein adsorbent which can selectively remove SAP proteins.

SUMMARY OF THE INVENTION

The present invention relates to an adsorbent for a serum amyloid protein, which comprises a water-insoluble carrier and a compound selected from the group consisting of a compound having an anionic functional group, a polyanionic compound having more than one anionic functional groups, aniline and an aniline derivative, said compound being immobilized onto said carrier, or and a group of the formula: $-NR^1R^2$ wherein $R^1$ is hydrogen atom, methyl group or ethyl group, and $R^2$ is an atomic group satisfying that the value of log P, in which P is a distribution coefficient in a water-octanol system, of a compound of the formula $R^2H$ is from 0 to 3.2, said group being bonded to said carrier.

Particularly, present invention relates to an adsorbent for serum amyloid A protein, which comprises a water-insoluble carrier and a polyanionic compound having more than one anionic functional groups immobilized onto said carrier; and adsorbent for serum amyloid A protein, which comprises a water-insoluble carrier and a compound selected from the group consisting of aniline and an aniline derivative immobilized onto said carrier; an adsorbent for serum amyloid A proteins, which comprises a water-insoluble carrier and a group of the formula: $-NR^1R^2$, wherein $R^1$ is hydrogen atom, methyl group or ethyl group, and $R^2$ is an atomic group satisfying that the value of log P, in which P is a distribution coefficient in a water-octanol system, of a compound of the formula $R^2H$ is from 0 to 3.2, said group being bonded to said carrier; and an adsorbent for serum amyloid P protein, which comprises a water-insoluble carrier and a compound having an anionic functional group, immobilized onto said carrier.

The adsorbent of the present invention is particularly suitable for removing or recovering serum amyloid A protein and serum amyloid P protein.

DETAILED DESCRIPTION

In the present invention, the term "body fluid" is blood, plasma, serum, ascites, lymph liquid, synovia in articular cavity, fractions thereof or any fluid components originated in a living body.

The water-insoluble carrier used in the present invention can be an inorganic carrier, an organic carrier consisting of synthetic high molecular compound or polysaccharide, and a complex carrier consisting of organic carrier and/or inorganic carrier from the point of the environment of SAA proteins existing in blood. It is preferable that the carrier has hydrophilic property and have little adsorption for the materials except the object materials, so-called non-specific adsorption. It is more preferable that there exist a functional group utilizable for immobilization onto the carrier or capable of being easily activated.

Typical examples of the above functional groups are amino group, carboxyl group, hydroxyl group, thiol group, aldehyde group, halogen group such as chloro group, acid anhydride group, amide group, ester group, epoxy group, silanol group, succinylimide group, and the like.

In the above case, typical examples of water-insoluble carrier preferably used in the present invention are, for instance, inorganic carriers such as glass beads and silica gel, organic carriers consisting of a synthetic high polymer compound such as cross-linked polyvinylalcohol, cross-linked polyacrylate or cross-linked polyamide or consisting of a polysaccharide such as cross-linked cellulose, crystalline cellulose, cross-linked agarose, cross-linked dextran, cross-linked chitin or cross-linked chitosan, organic-inorganic complex carrier that the surface of inorganic carrier such as glass beads are coated with a polysaccharide or high molecular compound, organic-organic complex carrier that the surface of organic carrier consisting of a synthetic high molecular compound are coated with polysaccharides, and the like. However, the present invention is not limited thereto. Among them, water-insoluble carrier consisting of a compound containing a hydroxy group is preferable from the point that it has a good biocompatibility and little adsorption for the materials except the object materials, so-called non-specific adsorption.

Though the water-insoluble carrier used in the present invention can be an inorganic carrier or an organic carrier from the point of the environment of SAP proteins existing in body fluid, it is preferable that the carrier have little non-specific adsorption. A hydrophilic water-insoluble carrier is more preferable than hydrophobic one since a hydrophilic carrier has less non-specific adsorption. And a water-insoluble carrier consists of a compound having a hydroxy group in its molecule is further more preferable.

In the above case, typical examples of the water-insoluble carrier used in the present invention are soft carriers such as agarose, dextran and polyacrylamide, inorganic carriers such as porous glass and porous silica gel, porous polymer hard gels made of synthetic high molecular compounds such as polymethylmethacrylate, polyvinyl alcohol and styrene-divinylbenzen copolymer and/or a natural high molecular compound such as cellulose. However, the present invention is not limited thereto.

With respect to the removing or recovering SAA proteins, the adsorbent of the present invention can be used for removing SAA proteins from a liquid containing various SAA proteins, for example, blood, blood serum, blood plasma, a diluted blood, a diluted blood serum, a diluted blood plasma, a liquid that the above liquid given a pretreatment such as removal of blood cells or removal of serum proteins, and the like. The adsorbent can be also used as an adsorbent for extracorporeal circulation treatment for secondary amyloidosis patients. For example, when the adsorbent of the present invention is used as an adsorbent for extracorporeal circulation treatment, the adsorbent is preferably an adsorbent having a sufficient mechanical strength for preventing consolidation. That is, the adsorbent of the present invention is preferably a "hard" adsorbent. Further, though the microstructure of the adsorbent of the present invention can be porous or non-porous, it is preferred that the adsorbent has a large specific surface area, i.e. has a porous structure, particularly a structure uniformly having pores at any part thereof.

The term "hard" in the present invention means, as shown in the Reference Example herein below, that the relation between a pressure drop and a flow rate determined by passing an aqueous fluid through a cylindrical column uniformly filled with the adsorbent keeps a linear relationship until the pressure drop is increased to 0.3 kg/cm². The term "porous" in the present invention means that the pore volume is not less than of the seeming volume of the adsorbent and the specific surface area is not less than 3 m²/g. Adsorbents not satisfying the above conditions have a too small adsorption capacity to be fit for a practical use. The examples of carriers used for the above adsorbent of the present invention are, for instance, porous vinyl materials such as porous cellulose gel, porous chitosan gel, styrene-divinylbenzene copolymer, cross-linked acrylate and cross-linked polyvinyl alcohol; inorganic porous materials made of glass, silica, alumina, and the like. However, the carriers used in the present invention are not limited thereto.

Further, in this case, when the adsorbent of the present invention has a porous structure, the pore size is required to be a size satisfying that SAA proteins having a molecular weight of 12,000 can easily enter the pore. Therefore it is important that the molecular weight of exclusion limit measured with a globular protein is not less than 12,000. Adsorbents having a molecular weight of exclusion limit of less than 12,000 tend to have a too small adsorption capacity and cannot be fit for a practical use. Further, it is preferred that the adsorbent has a molecular weight of exclusion limit of not less than $3 \times 10^5$ since SAA proteins easily diffuse into such a adsorbent.

On the other hand, the adsorbent having a molecular weight of exclusion limit more than $1 \times 10^8$ has a tendency that it cannot be fit for a practical use from reasons that its mechanical strength is too low, that its solid content is too low to achieve a sufficient adsorption capacity, and the like. Therefore, a molecular weight of exclusion limit is preferably not more than $1 \times 10^8$, and more preferably not more than $5 \times 10^7$.

The term "the molecular weight of the exclusion limit" means, for instance, as described in the literature such as "Jikken Kosoku Ekitai Chromatography (Experimental High Performance Liquid Chromatography)" written by Hiroyuki Hatano and Toshihiko Hanai, published by Kabushiki Kaisha Kagaku Dojin, the minimum molecular weight of the molecule which cannot permeate into a pore, i.e. which is excluded, in a gel permeation chromatography. Therefore, the molecular weight of exclusion limit is preferably $1.2 \times 10^4$ to $1 \times 10^8$.

Also as to removing and recovering SAP proteins, water-insoluble carriers used in the present invention preferably have porous structures, more preferably have continuous small pores with a large diameter. That is, it is necessary that SAP proteins easily enter the carrier for efficiently adsorbing SAP proteins which are formed with ten subunits and have a molecular weight of 230,000 to 250,000.

As a standard of diameter of pores in porous carrier, molecular weight of exclusion limit is usually employed, similarly to the above.

Therefore, the water-insoluble porous carrier used here preferably have a molecular weight of exclusion limit measured with a globular protein of not less than 230,000. Further, the molecular weight of exclusion limit is preferably not more than $1 \times 10^8$, and more preferably not more than $5 \times 10^7$, for the same reason as discussed above.

With respect to a porous structure of a water-insoluble carrier, a structure uniformly having pores at any part of the material is more preferable than a structure having pores only on the surface of the material. And it is preferred that a porosity of the material used in the present invention is not less than 20% in consideration of the capacity for the adsorption.

When the adsorbent of the present invention is adopted to the extracorporeal circulation treatment, it is necessary to flow a fluid having a high viscosity such as blood or plasma at a high flow rate. Therefore, it is desirable to use a hard water-insoluble carrier having a sufficient mechanical strength, so as to prevent consolidation of the adsorbents in a column.

That is, the term "hard" means, as shown in the Reference Example herein below, similarly to the description above, that the relation between a pressure drop and a flow rate determined by passing an aqueous fluid through a cylindrical column uniformly filled with the water-insoluble carrier keeps a linear relationship until the pressure drop is increased at least to 0.3 kg/cm$^2$.

A shape of a water-insoluble carrier can be optionally selected from shapes such as particle, sphere, fiber, sheet and hollow fiber. When a water-insoluble carrier with a shape of a particles is used, the particle size is preferably from 1 to 5000 μm. When the particles size is less than 1 μm, the pressure drop becomes large, and when the particle size is over 5,000 μm, the capacity becomes small.

In the present invention, any polyanionic compound can be used so long as the functional groups are charged with negative electricity in pH value around neutrality without any particular limitation.

Typical examples of the polyanionic compound are, for instance, a synthetic polyanionic compound such as polyacrylic acid, polyvinyl sulfonic acid, polyvinyl phosphoric acid, polystyrenesulfonic acid, polystyrenephosphoric acid, polyglutamic acid, polyaspartic acid, polymethacrylic acid, polyphosphoric acid or a styrene-maleic acid copolymer; a polysaccharide having anionic functional groups such as heparin, dextran sulfate, chondroitin, chondroitin sulfate, chitin or chitosan; and the like. The polyanionic compounds are not limited thereto. Among them, it is preferable to use a polyanionic compound having sulfate group.

Various methods can be used for introducing a polyanionic compound to immobilize the polyanionic compound onto at least a part of the surface of a water-insoluble carrier. An immobilizing method in which a strong covalent bond is formed is preferable.

As a compound having sulfate group among polyanionic compounds, a compound having a functional group utilizable for immobilization onto the water-insoluble carrier, besides the sulfate group, is preferable. Among them, partially sulfated polyhydric alcohols, and particularly sulfated saccharide (sulfated polysaccharide) are preferable, since they not only have both sulfate group and the functional group necessary for the immobilization but also are high in the biocompatibility and the activity, and further they can be easily immobilized onto the water-insoluble carrier. Also as to other polyanionic compounds, compounds having a functional group utilizable for immobilization besides anionic functional groups are preferable. Further, a SAA protein adsorbent comprising a water-insoluble carrier and more than one anionic functional group immobilized onto the carrier is particularly suitable for removing and recovering SAA protein.

Examples of aniline derivative in aniline and/or aniline derivative, which are used in the present invention, are N-monoalkylanilines such as N-methylaniline and N-ethyl-aniline; aromatic alkyl-substituted anilines such as o-toluidine, m-toluidine, p-toluidine, 2,3-xylidine and 2,4-xylidine; aromatic alkoxysubstituted-anilines such as o-aminoanisole, m-aminophenetole, p-aminoanisole, 2-aminophenetole, 3-aminophenetole and 4-aminophenetole; anilines having one or more substituent group consisting of one or more kinds of substituent groups on the aromatic ring, for instance, o-chloroaniline, m-chloroaniline, p-chloroaniline, o-nitroaniline, m-nitroaniline, p-nitroaniline, 2,4-dinitro-aniline, 2,6-dinitroaniline, 3,5-dinitroaniline, o-aminobenzoic acid, m-aminobenzoic acid, sodium p-aminobenzoate, ethyl o-aminobenzoate, ethyl m-aminobenzoate, ethyl p-aminobenzoate, o-aminobenzenesulfonic acid, m-aminobenzenesulfonic acid, p-aminobenzenesulfonic acid, sodium p-aminobenzensulfate, p-aminobenzensulfonamide, o-aminophenol, m-aminophenol, p-aminophenol, o-aminophenethyl alcohol, p-aminophenethyl alcohol, o-phenylenediamine, m-phenylenediamine, p-phenylenediamine, 2-aminotoluene-5-sulfonic acid, 3-aminotoluene-6-sulfonic acid, 4-amino-3-nitrobenzenesulfonic acid, sodium 2-amino-5-nitrobenzenesulfate, 2-amino-4-nitroanisole, 2-amino-4-nitrotoluene; and the like. The present invention is not limited thereto.

When aniline and the above aniline derivative are used, one kind of them or more than one kinds them can be used.

For immobilizing aniline and/or aniline derivative onto the water-insoluble carrier, various known methods can be employed without any specific limitation.

That is, a physical method, an ionic bonding method, covalent bonding method and the like can be employed. Since it is crucial that aniline and/or the aniline derivative immobilized are hardly released, the covalent bonding method which provides a firm bonding is preferably employed. With the other methods employed, it is preferable to make preventing the release. As occasion demands, a spacer may be introduced between the water-insoluble carrier and the aniline and/or aniline derivative.

A SAA protein adsorbent comprising a water-insoluble carrier and a compound selected from the group consisting of aniline and an aniline derivative immobilized onto the carrier is particularly suitable for removing or recovering SAA proteins.

The adsorbent of the present invention includes an adsorbent for SAA proteins, which comprises a water-insoluble carrier and a group of the formula: $-NR^1R^2$, wherein $R^1$ is hydrogenation, methyl group or ethyl group, and $R^2$ is an atomic group satisfying that the value of log P, in which P is a distribution coefficient in a water-octanol system, of a compound of the formula: $R^2H$ is from 0 to 3.2, said group being bonded to said carrier. This adsorbent is a water-insoluble matrix having, on at least a part of the surface thereof, a group of the formula: $-NR^1R^2$, wherein $R^1$ is hydrogen atom, methyl group or ethyl group, and $R^2$ is an atomic group satisfying that the value of log P, in which P is a distribution coefficient in a water-octanol system, of a compound of the formula: $R^2H$ is from 0 to 3.2.

The logarithm of a partition coefficient in an water-octanol system, i.e. log P, is a hydrophobic parameter of a compound. The distribution coefficient P is obtained according to the following typical method.

First of all, a compound is dissolved in an octanol (or a water) and an equal volume of a water (or an octanol) is added thereto. After shaking for 30 minutes by Griffin flask shaker (made by Griffin & George Ltd.), it is centrifuged for from 1 to 2 hours at 2000 rpm. Then concentrations of the compound in both octanol and water layers are measured by various methods such as spectroscopic method and GLC, and the value of P is obtained according to the following formula:

$$P = Coct/Cw$$

Coct: a concentration of a compound in an octanol layer

Cw: a concentration of a compound in a water layer

Until now, many investigators have measured log P of various compounds and the found values were put in order by C. Hansch et. al. ["PARTITION COEFFICIENTS AND THEIR USES", Chemical Reviews, 71, 525 (1971)]. As to the compounds whose found values are unknown, the calculated values using a hydrophobic fragmental constant f (such value hereinafter referred to as "rf"), shown in "THE HYDROPHOBIC FRAGMENTAL CONSTANT" (Elsevier Sci. Pub. Com., Amsterdam, 1977) written by R. F. Rekker, can be a good guide.

A hydrophobic fragmental constant show the hydrophobicity of various fragments, which are determined by a statistical management of many found values of log P, and the total of f of each fragment which is a constituent of one compound almost corresponds to log P.

The hydrophobic property of the atomic group $-R^2$ of the group $-NR^1R^2$ existing in the adsorbent of the present invention, plays an important role in the adsorption of SAA proteins. In case that the value of log P of $R^2H$ is less than 0, a hydrophobic interaction with SAA proteins is so weak that a capacity for adsorption of SAA proteins is low. On the contrary, in case that the value of log P is more than 3.2, there is a problem in point of selectivity because not only SAA proteins but also HDL and any other proteins are adsorbed. That is, for a good adsorption capacity and a good selectivity, the value of log P of a compound of the formula $R^2H$ wherein $R^2$ is an atomic group in the adsorbent of the present invention is from 0 to 3.2.

Also, as to the group $-NR^1R^2$ existing on at least a part of the surface of water-insoluble matrix in the present invention, any group $-NR^1R^2$ can be used without particular limitation as far as the group satisfies that the value of log P of the compound of $R^2H$ wherein $R^2$ is an atomic group in the $-NR^1R^2$ is from 0 to 3.2.

Moreover, as the group $-NR^1R^2$ which is existing on the adsorbent of the present invention, one or more kinds thereof can be employed.

Also, the adsorbent of the present invention, which comprises a water-insoluble carrier and a group $-NR^1R^2$ bonded to the carrier is distinguished according to the process for preparation as described below. Both of them can be adaptable to the present invention.

(1) The adsorbent obtained by introducing the group $-NR^1R^2$ into a water-insoluble carrier.

(2) The adsorbent obtained by introducing the group $-NR^1R^2$ into a water-soluble high molecular compound, and then subjecting them a treatment such as cross-linking to give a water-insoluble matrix.

As the water-insoluble carrier used in the above process (1), water-insoluble carriers described above can be used.

Typical examples of water-soluble high molecular compound used for preparation of the adsorbent in the above process (2) are polysaccharides such as dextran and starch, high molecular compound such as polyvinyl alcohol and saponificating product of ethylene-vinyl acetate copolymer having a small content of ethylene. However, the present invention is not limited thereto.

During the process for preparation of both adsorbents of the above processes (1) and (2), the group $-NR^1R^2$ is introduced into a water-insoluble carrier or a water-soluble high molecular compound. In the present invention, it is preferable that the group $-NR^1R^2$ is bonded to a water-insoluble carrier or a water-soluble high molecular compound by a covalent bond because of a small possibility of release of ligands.

The nitrogen atom existing in the group $-NR^1R^2$ in the adsorbent of the present invention can be derived from either a water-insoluble carrier, a water-soluble high molecular compound or a ligand.

In other words, there are some methods to introduce a group $-NR^1R^2$ into either a water-insoluble carrier or a water-soluble high molecular compound; one is that the group $-NR^1R^2$ is a group derived from a compound of the formula $HNR^1R^2$, wherein $R^2$ and $R^2$ are as defined above, and bonded to a water-insoluble carrier or a water-soluble high molecular compound by reacting the compound $HNR^1R^2$ and a water-insoluble carrier or a water-soluble high molecular compound to combine nitrogen atom of the above compound with a water-insoluble carrier or water-soluble high molecular compound and another is that the group $-NR^1R^2$ is introduced into a water-insoluble carrier or a water-soluble high molecular compound by reacting a water-insoluble carrier or a water-soluble high molecular compound having a group of the formula: —NHR$^1$, wherein R$^1$ is defined above, with a compound of the formula: R$^2$X, wherein R$^2$ is as defined above and X is a functional group capable of reacting with amino group or a part of the functional group. Both of them are available in the present invention.

The term "a water-insoluble carrier having the group —NHR$^1$" in the above is a water-insoluble carrier consisting of a material originally having —NHR$^1$ group such as chitin and chitosan, or a water-insoluble carrier prepared by introducing the group —NHR$^1$ into a water-insoluble carrier originally having no amino group by activating the carrier with cyanogen bromide, epichlorohydrin, 1,4-butanediol diglycidyl ether and the like and then reacting the carrier with the compound of either the formula H$_2$NR$^1$, wherein R$^1$ is as defined above, or the formula HNR$^1$R$^3$, wherein R$^1$ is as defined above and R$^3$ is an atomic group having a functional group capable of binding to a carrier.

When the group —NR$^1$R$^2$ is introduced into a water-insoluble carrier or a water-soluble high molecular compound, in case of bonding the compound HNR$^1$R$^2$ via amino group to a water-insoluble carrier or a water-soluble high molecular compound, aniline, an aniline derivative, a mixture of aniline and an aniline derivative, benzylamine, benzylamine derivative and a mixture of benzylamine and benzylamine derivative are particularly useful as a compound of HNR$^1$R$^2$ Examples of the aniline derivative are, for instance, N-monoalkylanilines such as N-methylaniline and N-ethyl-aniline; aromatic alkyl-substituted anilines such as o-toluidine, m-toluidine, p-toluidine, 2,3-xylidine and 2,4-xylidine; aromatic alkoxysubstituted-anilines such as o-aminoanisole, m-aminoanisole, p-aminoanisole, 2-aminophenetole, 3-aminophenetole and 4-aminophenetole; anilines having one or more substituent group consisting of one or more kinds of substituent groups on the aromatic ring, for instance, o-chloroaniline, m-chloroaniline, p-chloroaniline, o-nitroaniline, m-nitroaniline, p-nitroaniline, 2,4-dinitroaniline, 2,6-dinitroaniline, 3,5-dinitroaniline, o-aminobenzoic acid, m-aminobenzoic acid, p-aminobenzoic acid, ethyl o-aminobenzoate, ethyl m-aminobenzoate, ethyl p-aminobenzoate, p-aminobenzensulfonamide, o-aminophenol, m-aminophenol, p-aminophenol, o-aminophenethyl alcohol, p-aminophenethyl alcohol, o-phenylenediamine, m-phenylenediamine, p-phenylenediamine, 2-amino-4-nitroanisole, 2-amino-4-nitrotoluene and the like. The present invention is not limited thereto. Moreover, examples of the compound having the formula: HNR$^1$R$^2$ are, for instance, monoalkylamines such as n-propylamine, n-butylamine and n-pentylamine, dialkylamines, a mixture thereof, and the like. The present invention is not limited the above examples.

In case group —NR$^1$R$^2$ is bonded to a water-insoluble carrier or water-soluble high molecular compound by reacting a water-insoluble carrier or a water-soluble high molecular compound with a compound R$^2$X, examples of the compound R$^2$X are, for instance, carboxylic acids such as n-butanoic acid, n-pentanoic acid, benzoic acid and phthalic acid, and the like. However, the present invention is not limited to the above examples.

Also, a SAA protein adsorbent which comprises a water-insoluble carrier and a group of the formula: —NR$^1$R$^2$, wherein R$^1$ is hydrogen atom, methyl group or ethyl group, and R$^2$ is an atomic group satisfying that the value of log P, in which P is a distribution coefficient in a water-octanol system, of a compound of the formula: R$^2$H is from 0 to 3.2, said group being bonded to said carrier is particularly suitable for removing or recovering SAA proteins.

The adsorbent of the present invention also includes an adsorbent comprising a water-insoluble carrier and compounds having anionic functional groups immobolized onto the carrier.

In the present invention, any anionic functional groups can be used so long as the functional groups are charged with negative electricity in pH value around neutrality. Typical examples of the anionic functional group are, for instance, carboxyl group, sulfonic acid group, sulfonate group, sulfate group, silanol group, phosphate group, phenolic hydroxyl group, and the like, but the groups are not limited thereto.

Among them, carboxyl group, sulfonic acid group, sulfate group, phosphate group are preferred in that they have excellent affinity to SAP proteins.

As the compound having the anionic functional group, there can be used both a monoanionic compound which has one anionic functional group in its molecule and a polyanionic compound which has more than one anionic functional groups. The polyanionic compound is preferable because it has an excellent affinity to SAP proteins, and a lot of the anionic functional groups are easily introduced into a unit of the porous material. The polyanionic compound having a molecular weight of not less than 1,000 is especially preferable from the point of the affinity and the quantity of the anionic functional groups introduced. The anionic functional groups in a polyanionic compound may be the same or different.

Typical examples of the polyanionic compound are, for instance, a synthetic polyanionic compound such as polyacrylic acid, polyvinyl sulfuric acid, polyvinyl sulfonic acid, polyvinyl phosphoric acid, polystyrenesulfonic acid, polystyrenephosphoric acid, polyglutamic acid, polyaspartic acid, polymethacrylic acid, polyphosphoric acid or a styrene-maleic acid copolymer; a polysaccharide having anionic functional groups such as heparin, dextran sulfate, chondroitin, chondroitin sulfate, phosphomannan, chitin or chitosan; and the like. The polyanionic compounds are not limited thereto.

Both of the same or different kinds of the compounds having the anionic functional groups can be immobilized in the adsorbent of the present invention.

The adsorbent of the present invention is in a state that compounds having anionic functional groups are immobilized onto a water-insoluble carrier. For obtaining such state that compounds having anionic functional groups are immobilized, there are various methods for introducing the anionic functional groups into the adsorbent and any methods can be applied to the invention. As methods for introducing the anionic functional group into the adsorbent, there are exemplified, for instance, (1) a method in which monomers or crosslinking agents having the anionic functional group or a group capable of easily converting into the anionic functional group are polymerized to form the adsorbent, (2) a method in which the anionic functional group-containing compound is immobilized onto a water-insoluble carrier, (3) a method in which a compound capable of forming the anionic functional group is directly reacted with a water-insoluble carrier to immobilize a compound having the anionic functional group onto the water-insoluble carrier, and the like.

Of course, the anionic functional group-containing compound having the anionic functional group in itself such as glass, silica and alumina may be used as the adsorbent.

In the method (1), examples of the monomers or crosslinking agents having the anionic functional group or a group capable of easily converting into the anionic functional group are, for instance, acrylic acid, acrylic acid ester, methacrylic acid, methacrylic acid ester, styrenesulfonic acid, and the like, but the monomers or crosslinking agents are not limited thereto.

In the process (2), the anionic functional group-containing compound is immobilized onto the water-insoluble carrier by any methods, for example, physical adsorption, ionic bond, covalent bond, and the like. In case of using the adsorbent for a medical treatment, it is important that the anionic functional groups are not eliminated from the adsorbent during the sterilization or the treatment. Accordingly, it is desirable, for the above-mentioned purpose, to use the adsorbent obtained by the method capable of forming a covalent bond which is able to firmly immobilize the functional group onto the carrier.

When the compound having an anionic functional group is immobilized onto the water-insoluble carrier by a covalent bond, it is more preferable to use the compound having a functional group utilizable for the immobilization onto the carrier, besides the anionic functional group.

Examples of the functional group utilizable for the immobilization are, for instance, amino group, amide group, carboxyl group, acid anhydride group, succinylimide, hydroxyl group, thiol group, aldehyde group, halogen group, epoxy group, silanol group, and the like. The functional groups are not limited thereto.

There exist a lot of compounds which have both the anionic functional groups and the above-mentioned functional groups utilizable for the immobilization. As these compounds, there is exemplified taurine, sulfanilic acid, glycine, phosphoryl ethanolamine, L-tyrosine.

As compounds having sulfate group among the anionic functional group-containing compound, there are exemplified, for instance, sulfuric acid esters of hydroxyl group-containing compounds such as alcohol, saccharides and glycol. Among the above anionic functional group-containing compounds, partially sulfated polyhydric alcohols, and particularly sulfated saccharide are preferable, since the sulfuric acid esters not only have both sulfate group and the functional group necessary for the immobilization but also are high in the biocompatibility and the activity. A sulfated polysaccharide is especially preferable since it can be easily immobilized onto the water-insoluble carrier.

As the representative example of the method (3), that is, a method in which a compound capable of forming the anionic functional group is directly reacted with a water-insoluble carrier to introduce the anionic functional group into the carrier, there are, for instance, a method in which sulfate group is introduced into a carrier having hydroxyl group, and the like. In such a case, sulfate group can be directly introduced into the adsorbent by reacting a reagent such as chlorosulfonic acid or concentrated sulfuric acid with the water-insoluble carrier having hydroxyl group.

The adsorbent comprising a water-insoluble carrier and anionic functional groups immobilized onto the carrier is particularly suitable for removing or recovering SAP proteins.

A shape of the present invention can be selected from any shapes such as a particle, fiber, sheet and hollow fiber. And the microstructure of the adsorbent can be porous or non-porous. However, the adsorbent of the present invention has preferably a large specific surface area, i.e. has a porous structure, in order to obtain a high adsorbability per unit.

There are various methods for removing SA proteins particularly SAA proteins and SAP proteins from body fluid and any methods can be used.

A method for removing a serum amyloid protein, which comprises passing body fluid containing a serum amyloid protein through a removing apparatus, said apparatus comprising a container having a fluid inlet and a fluid outlet, at least one filter through which a fluid and components included in the fluid can pass while the adsorbent of the present invention cannot pass at the fluid outlet side, and the adsorbent packed in said container, is preferred because this method is convenience.

According to the present invention, SA proteins, particularly SAA proteins and SAP proteins can be selectively removed from body fluid without decreasing HDL largely. Besides, the adsorbent can be provided at a low cost.

The present invention is more specifically described and explained by the following Reference Example, Preparation Examples, Examples and Comparative Examples in which all % are by weight otherwise noted. It is to be understood that the present invention is not limited to the Examples and various changes and modifications can be made without departing from the scope and spirit of the present invention.

REFERENCE EXAMPLE

A relation between a flow rate and a pressure drop $\Delta P$ was determined by passing water by means of a peristartic pump through cylindrical glass columns equipped at both ends with filters having a pore size of 15 μm (inner diameter: 9 mm, column length: 150 mm), in which an agarose gel (Biogel A5m made by Biorado Co., particle size: 50 to 100 mesh), a polymer hard gel (Toyopearl HW 65 made by TOSOH CO., LTD., particle size: 50 to 100 μm) and a porous cellulose gel (Cellulofine GC 700 made by Chisso Corporation, particle size: 45 to 105 μm) were packed respectively. The results are shown in FIG. 1.

Figure 1:
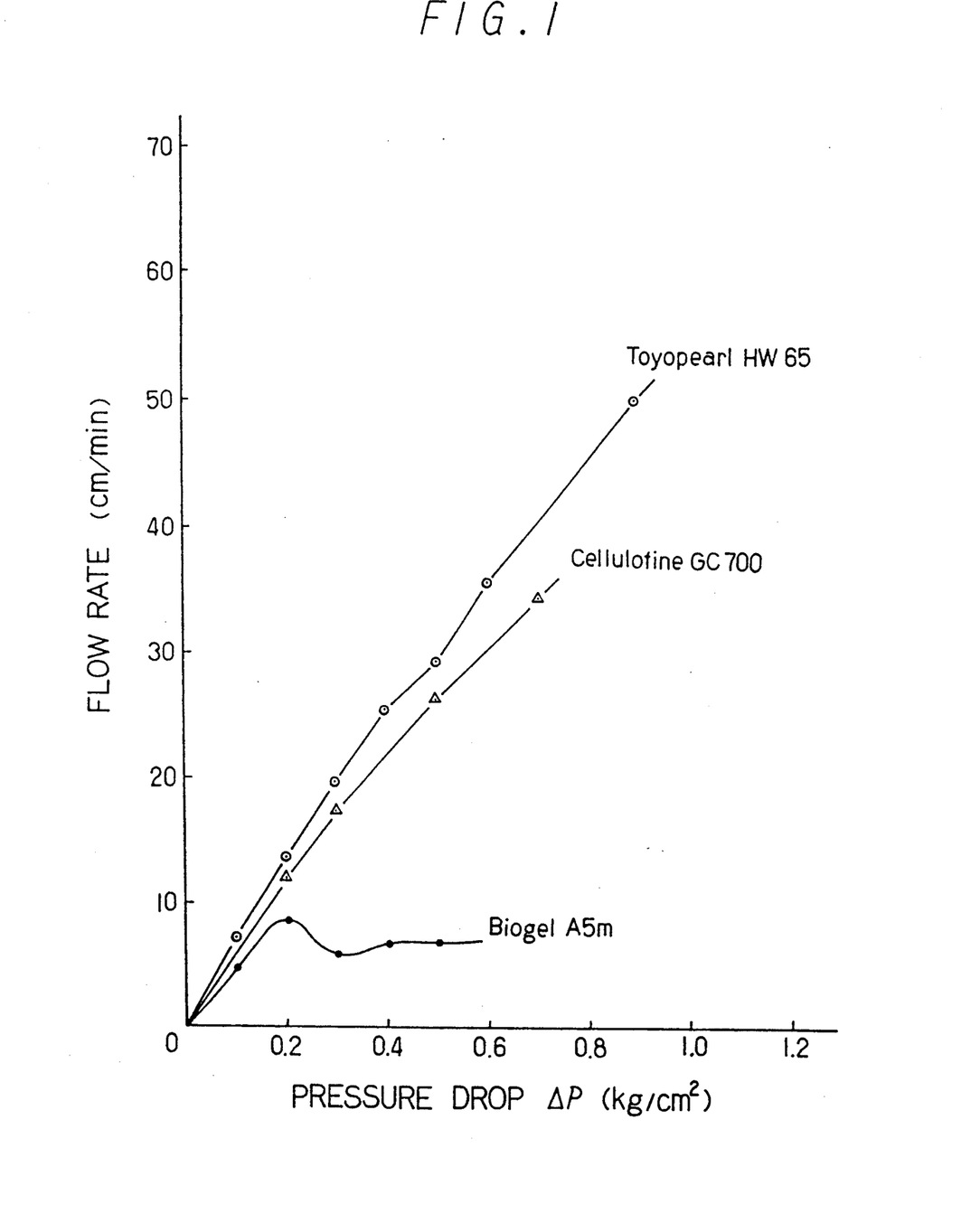
FIG. 1 is a graph showing a relation between a flow rate and a pressure drop $\Delta p$ obtained in Reference Example, mentioned later.

As shown in FIG. 1, an increase of a flow rate is nearly proportional to that of a pressure drop in case of hard gels, i.e. Toyopearl and Cellulofine, whereas in case of soft gel, i.e. the agarose gel, consolidation occurs and a flow rate does not increase even if a pressure drop increases.

PREPARATION EXAMPLE 1

To 100 ml of a porous cellulose gel (commercially available under the trade name "CK gel A3" made by Chisso Corporation, exclusion limit of globular proteins: $5 \times 10^7$, particle size: 63 to 125 μm) were added 100 ml of water, 53 ml of 2N aqueous solution of sodium hydroxide and 18 ml of epichlorohydrin, and the mixture was stirred at 40° C. for 2 hours. After the reaction was completed, the gel was filtered off from the reaction mixture and was washed with water to give an epoxidated CK gel A3.

EXAMPLE 1

After 46.5 g of sodium dextran sulfate and a small amount of water were added to 100 ml of the obtained epoxidated CK gel A3 to dissolve the gel thoroughly, water was added thereto so that the total amount was adjusted to 177 ml. The mixture was adjusted to pH 9.2 by adding 2N aqueous solution of sodium hydroxide and allowed to stand at 45° C. for 16 hours. After the reaction was completed, the gel was filtered off from the reaction mixture, and washed with water to give a CK gel A3 with immobilized dextran sulfate.

There was taken 0.4 ml of the gel with immobilized dextran sulfate to a test tube, to which 2.4 ml of human serum including SAA protein was added. After shaking the mixture at 37° C. for 2 hours, concentration of SAA protein in the supernatant was measured. Also, for examining the selectivity of the adsorbent, concentration of HDL cholesterol in the supernatant is measured.

The results are shown in Table 1.

Measurement of Concentration of SAA Protein

The concentration of SAA protein in the supernatant is measured according to enzyme linked immunosorbent assay (ELISA Method). Briefly, a diluted antibody to SAA (available from Hoechst Corporation) is dropped on a plate and the antibody is fixed to the plate by allowing the plate to stand at 4° C. for 12 hours.

A diluted sample and standard serum are dropped respectively, on the plates, and antigen-antibody reaction is caused by allowing the plates to stand at room temperature for 3 hours. Then, peroxidase conjugated anti-SAA antibody is added to the plates to conduct antigen-antibody reaction at room temperature for 3 hours. After washing the plate, the enzyme reaction is conducted and the absorbance using chromatoscanner ("CS-930" made by Shimadzu Corporation) at the wave length of 492 μm. The concentration of SAA protein in the sample is found from the results of the measurements as to the sample and standard serum, with regarding the value of the concentration of SAA in the standard serum as 1.

PREPARATION EXAMPLE 2

The procedure of Preparation Example 1 was repeated except that 100 ml of a porous cellulose gel (commercially available under the trade name "CK gel A22" made by Chisso Corporation, exclusion limit of globular proteins: $3 \times 10^7$, particle size: 53 to 125 μm) was used instead of CK gel A3 to give a epoxidated CK gel A22.

EXAMPLE 2

The procedure of Example 1 was repeated except that the epoxidated CK gel A22 obtained in Preparation Example 2 was used to give a CK gel A22 with immobilized dextran sulfate.

The obtained CK gel A22 with immobilized dextran sulfate was treated in the same manner as in Example 1 and the concentrations of SAA protein and HDL cholesterol were measured in the same manner as in Example 1.

The results are shown in Table 1.

EXAMPLE 3

To 100 ml of the epoxidated CK gel A3 obtained in Preparation Example 1 was added 15.6 g of polyacrylic acid having an amino group at one side of the polymer ends, and thereto water was added to give a solution with the total amount of 156 ml. After the solution was mixed thoroughly by shaking and allowed to stand at 50° C. for 10 hours. After the reaction was completed, the gel was filtered off from the reaction mixture and washed with water to give a CK gel A3 with immobilized polyacrylic acid.

The obtained gel with immobilized polyacrylic acid was treated in the same manner as in Example 1, and the concentrations of SAA protein and HDL cholesterol were measured in the same manner as in Example 1.

The results are shown in Table 1.

COMPARATIVE EXAMPLE 1

A supernatant was obtained in the same manner as in Example 1 except that 0.24 ml of physiological saline was used instead of 0.4 ml of the CK gel A3 with immobilized dextran sulfate. The concentrations of SAA protein and HDL cholesterol in the supernatant were measured in the same manner as in Example 1.

The results are shown in Table 1.

TABLE 1

| Ex. No. | Concentration of SAA protein (with regarding the concentration of SAA protein in standard serum as 1) | Concentration of HDL cholesterol (mg/dl) |
|---|---|---|
| 1 | 0.086 | 12 |
| 2 | 0.086 | 13 |
| 3 | 0.119 | 5 |
| Com. Ex. | | |
| 1 | 0.273 | 15 |

From the results shown in Table 1, it is confirmed that when the adsorbent of the present invention is used, HDL is hardly adsorbed while SAA protein is adsorbed.

PREPARATION EXAMPLE 3

To 10 ml of CK gel A3 were added 10 ml of water, 5.4 ml of 2N aqueous solution of sodium hydroxide and 1.9 ml of epichlorohydrin, and the mixture was stirred at 40° C. for 2 hours. After the reaction was completed, the gel was filtered off from the reaction mixture and was washed with water to give an epoxidated gel.

EXAMPLE 4

After 8 ml of water and 120 mg of aniline were added to 10 ml of the obtained epoxidated gel, the mixture was thoroughly mixed and reacted while allowing to stand at 50° C. for 6 hours. After the reaction was completed, the gel was filtered off from the reaction mixture and washed with water to give a gel with immobilized aniline.

There was taken 0.4 ml of the gel with immobilized aniline to a test tube, to which 2.4 ml of human serum including SAA protein was added. After shaking the mixture at 37° C. for 2 hours, the concentrations of SAA protein and HDL cholesterol in the supernatant were measured in the same manner as in Example 1.

The results are shown in Table 2.

EXAMPLE 5

To 10 ml of the epoxidated gel obtained in Preparation Example 3, were added 10 ml of water and 57 mg of hexamethylenediamine, and the mixture was thoroughly mixed. The mixture was reacted while allowing to stand at 40° C. for 2 days. After the reaction was completed, the gel was filtered off from the reaction mixture and washed with water to give an aminated gel (hereinafter referred to as "N-gel").

After 10 ml of the obtained N-gel was washed on a glass filter, firstly with 50 ml of 10% (by volume) solution of triethylamine in dioxane, and secondly with 100 ml of dioxane, the gel was put into a reactor. There was added 90 mg of benzoic acid in 25 ml of dioxane to the reactor, to which 100 mg of dicyclohexylcarbodiimide in 2 ml of dioxane was added with stirring. After the mixture was reacted with stirring for 3 hours, 100 mg of dicyclohexylcarbodiimide in 2 ml of dioxane was added thereto, then the reaction was continued for 3 hours with stirring. After the reaction was completed, the gel was filtered off from the reaction mixture and washed with, in the order of dioxane, methanol, dioxane and water to give a N-gel with immobilized benzonic acid.

The obtained gel was treated in the same manner as in Example 1 and the concentrations of SAA protein and HDL cholesterol were measured in the same manner as in Example 1.

The results are shown in Table 2.

COMPARATIVE EXAMPLE 2

There was added 40 mg of n-octylamine to 10 ml of the epoxydated gel obtained in Preparation Example 4, and the reaction was carried out by allowing the mixture to stand at room temperature for 6 days in 50% (by/volume) aqueous solution of ethanol. After the reaction was completed, the gel was filtered off from the reaction mixture and washed thoroughly with 50% (by/volume) aqueous solution of ethanol, and with water to give a gel with immobilized n-octylamine.

The obtained gel was treated in the same manner as in Example 1, and the concentrations of SAA protein and HDL cholesterol were measured in the same manner as in Example 1.

The results are shown in Table 2.

COMPARATIVE EXAMPLE 3

A supernatant was obtained in the same manner as in Example 1, except that 0.24 ml of physiological saline was used instead of the gel with immobilized aniline obtained in Example 4. With respect to the obtained supernatant, the concentrations of SAA protein and HDL cholesterol were measured in the same manner as in Example 1.

The results are shown in Table 2.

TABLE 2

| Ex. No. | Concentration of SAA protein (With regarding the concentration of SAA protein in standard serum as 1) | Concentration of HDL cholesterol (mg/dl) |
|---|---|---|
| 4 | 0.030 | 13 |
| 5 | 0.023 | 14 |
| Com. Ex. | | |
| 2 | 0.023 | 0 |
| 3 | 0.065 | 15 |

From the results shown in Table 2, it is confirmed that when the adsorbent of the present invention is used, HDL is hardly adsorbed while SAA protein is adsorbed.

PREPARATION EXAMPLE 4

To 10 ml of CK gel A3 were added 10 ml of water, 5.4 ml of 2N aqueous solution of sodium hydroxide and 1.9 ml of epichlorohydrin, and the mixture was stirred at 40° C. for 2 hours. After the reaction was completed, the gel was filtered off from the reaction mixture and was washed with water to give an epoxidated gel.

EXAMPLE 6

After 8 ml of water and 120 mg of aniline were added to 10 ml of the obtained epoxidated gel, the mixture was thoroughly mixed, and the mixture was reacted at 50° C. for 6 hours while allowing to stand. After the reaction was completed, the gel was filtered off from the reaction mixture and washed with water to give a gel with immobilized aniline.

The group immobilized to the CK gel A3 is represented by the formula: $-NR^1R^2$ in which $R^1$ is hydrogen atom and $R^2$ is phenyl group. The value of log P of the compound having the formula: $R^2H$ in which $R^2$ is phenyl group is shown in Table 3.

There was taken 0.4 ml of the gel with immobilized aniline to a test tube, to which 2.4 ml of human serum including SAA protein was added. After shaking the mixture at 37° C. for 2 hours, the concentrations of SAA protein and HDL cholesterol in the supernatant were measured in the same manner as in Example 1.

The results are shown in Table 3.

EXAMPLE 7

To 10 ml of the epoxidated gel obtained in Preparation Example 4, were added 10 ml of water and 57 mg of hexamethylenediamine, and the mixture was thoroughly mixed. The mixture was reacted while allowing to stand at 40° C. for 2 days. After the reaction was completed, the gel was filtered off from the reaction mixture and washed with water to give an aminated gel (hereinafter referred to as "N-gel").

After 10 ml of the obtained N-gel was washed on a glass filter, firstly with 50 ml of a 10% (by volume) solution of triethylamine in dioxane, and secondly with 100 ml of dioxane, the gel was put into a reactor. There was added 90 mg of benzoic acid in 25 ml of dioxane to the reactor, to which 100 mg of dicyclohexylcarbodiimide in 2 ml of dioxane was added with stirring. After the mixture was reacted with stirring for 3 hours, 100 mg of dicyclohexylcarbodiimide in 2 ml of dioxane was added thereto, then the reaction was continued for 3 hours with stirring. After the reaction was completed, the gel was filtered off from the reaction mixture and washed with, in the order of dioxane, methanol, dioxane and water, to give a N-gel with immobilized benzoic acid.

The group immobilized to the CK gel A3 is represented by the formula: $-NR^1R^2$ in which $R^1$ is hydrogen atom and $R^2$ is 1-phenylhexyl group. The value of log P of the compound having the formula: $R^2H$ in which $R^2$ is 1-phenylhexyl group is shown in Table 3.

The obtained gel was treated in the same manner as in Example 1 and the concentrations of SAA protein and HDL cholesterol were measured in the same manner as in Example 1.

The results are shown in Table 3.

EXAMPLE 8

To 10 ml of the epoxidated gel obtained in Preparation Example 4 was added 155 mg of n-butylamine, which was reacted in 50% (by/volume) aqueous solution of ethanol at room temperature for 6 days while allowing to stand. After the reaction was completed, the gel was filtered off from the reaction mixture and was washed thoroughly with 50% (by/volume) aqueous solution of ethanol, and then with water to give a gel with immobilized n-butylamine.

The group immobilized to the CK gel A3 is represented by the formula: $-NR^1R^2$ in which $R^1$ is hydrogen atom and $R^2$ is n-butyl group. The value of log P of the compound having the formula: $R^2H$ in which $R^2$ is n-butyl group is shown in Table 3.

The obtained gel was treated in the same manner as in Example 1 and the concentrations of SAA protein and HDL cholesterol were measured in the same manner as in Example 1.

The results are shown in Table 3.

EXAMPLE 9

The procedure of Example 8 was repeated except that 227 mg of benzylamine was used instead of 155 mg of n-butylamine to give a gel with immobilized benzylamine.

The group immobilized to the CK gel A3 is represented by the formula: $-NR^1R^2$ in which $R^1$ is hydrogen atom and $R^2$ is benzyl group. The value of log P of the compound having the formula: $R^2H$ in which $R^2$ is benzyl group is shown in Table 3.

The obtained gel was treated in the same manner as in Example 1 and the concentrations of SAA protein and HDL cholesterol were measured in the same manner as in Example 1.

The results are shown in Table 3.

COMPARATIVE EXAMPLE 4

The procedure of Example 8 was repeated except that 273 mg of n-octylamine was used instead of 155 mg of n-butylamine to give a gel with immobilized n-octylamine.

The group immobilized to the CK gel A3 is represented by the formula: $-NR^1R^2$ in which $R^1$ is hydrogen atom and $R^2$ is n-octyl group. The value of log P of the compound having the formula: $R^2H$ in which $R^2$ is n-octyl group is shown in Table 3. The obtained gel was treated in the same manner as in Example 1 and the concentrations of SAA protein and HDL cholesterol were measured in the same manner as in Example 1.

The results are shown in Table 3.

COMPARATIVE EXAMPLE 5

The procedure of Example 8 was repeated except that 510 mg of cetylamine was used instead of 155 mg of n-butylamine to give a gel with immobilized cetylamine.

The group immobilized to the CK gel A3 is represented by the formula: $-NR^1R^2$ in which hydrogen atom and $R^2$ is cetyl group. The value of log P of the compound having the formula: $R^2H$ in which $R^2$ is cetyl group is shown in Table 3.

The obtained gel was treated in the same manner as in Example 1 and the concentrations of SAA protein and HDL cholesterol were measured in the same manner as in Example 1.

The results are shown in Table 3.

COMPARATIVE EXAMPLE 6

The procedure of Example 8 was repeated except that 384 mg of L-tyrosine was used instead of 155 mg of n-butylamine to give a gel with immobilized L-tyrosine.

The group immobilized to the CK gel A3 is represented by the formula: $-NR^1R^2$ in which $R^1$ is hydrogen atom and $R^2$ is 1-carboxy-2-(p-hydroxyphenyl)-ethyl group. The value of log P of the compound having the formula: $R^2H$ in which $R^2$ is 1-carboxy-2-(p-hydroxyphenyl)ethyl group is shown in Table 3.

The obtained gel was treated in the same manner as in Example 1 and the concentrations of SAA protein and HDL cholesterol were measured in the same manner as in Example 1.

The results are shown in Table 3.

COMPARATIVE EXAMPLE 7

A supernatant was obtained in the same manner as in Example 1 except that 0.24 ml of physiological saline was used instead of the gel with immobilized aniline obtained in Example 6. With respect to the obtained supernatant, the concentrations of SAA protein and HDL cholesterol were measured in the same manner as in Example 1.

The results are shown in Table 3.

TABLE 3

| Ex. No. | Log P in $R^2H$ | Concentration of SAA protein (With regarding the concentration of SAA protein in standard serum as 1) | Concentration of HDL cholesterol (mg/dl) |
|---|---|---|---|
| 6 | 2.1 | 0.030 | 13 |
| 7 | 1.5 | 0.023 | 14 |
| 8 | 2.5 | 0.041 | 14 |
| 9 | 2.7 | 0.055 | 14 |
| Com. Ex. | | | |
| 4 | 4.6 | 0.023 | 0 |
| 5 | 8.8 | 0.045 | 0 |
| 6 | −1.8 | 0.087 | 14 |
| 7 | — | 0.082 | 15 |

From the results shown in Table 3, it is confirmed that when the adsorbent of the present invention is used, HDL is hardly adsorbed while SAA protein is adsorbed.

EXAMPLE 10

To 5 ml of the epoxidated gel obtained in Preparation Example 1 was added a solution prepared by dissolving 0.17 g of sulfanilic acid in 10 ml of water and adjusting the pH value to 9.9, and the mixture was shaken for 24 hours at room temperature. The unreacted epoxy group in the gel was blocked by adding 0.5% aqueous solution of monoethanolamine to the gel and shaking to give a cellulose gel with immobilized sulfanilic acid.

EXAMPLE 11

To 5 ml of the epoxidated gel obtained in Preparation Example 1 were added 4 g of sodium dextran sulfate (molecular weight: about 5,000, sulfer content: 18%) and 5 ml of water. The pH of the mixture was adjusted to pH 9 and the mixture was shaken at 45° C. for 16 hours. Then, the gel was filtered off from the reaction mixture and was washed, first, with 2M aqueous solution of sodium chloride, and secondly with 0.5M aqueous solution of sodium chloride, and finally with water. The unreacted epoxy group in the gel was blocked by adding 0.5% aqueous solution monoethanolamine to the gel and shaking to give a cellulose gel with immobilized dextran sulfate.

PREPARATION EXAMPLE 5

There was prepared a suspension of 40 ml of CK gel A3 in heptane with the total volume of 70 ml. To the suspension were added 10 ml of 20% NaOH and 40 drops (2.0 ml) of the nonionic surfactant TWEEN 20 (a commercially available polyoxyethylene sorbitan monolaurate made by Bio-Rad Laboratories), and the mixture was shaken at 40° C. for 30 minutes. Then, 10 ml of epichlorohydrin was added thereto and the mixture was shaken at 40° C. for 6 hours. After the reaction was completed, the gel was filtered off from the reaction mixture and washed with ethanol first, and then with water to give an epoxidated gel.

EXAMPLE 12

To 10 ml of the epoxidated gel obtained in Preparation Example 5 was added a solution of 1 g of polyacrylic acid having an amino group at one side of the polymer ends (molecular weight: about 1,000) in 5 ml of water, to which 1 ml of 2M NaOH was added, and then the mixture was allowed to stand at room temperature for 48 hours. After the reaction was completed, the gel was filtered off from the reaction mixture and washed with water to give a cellulose gel with immobilized polyacrylic acid.

The polyacrylic acid having an amino group at one side of the polymer ends was obtained by low polymerization reaction of acrylic acid using 2-aminoethanethiol as a chain transfer agent and azobisisobutyronitrile (AIBN) as an initiator (Teruo Okano, et al. (1977), "Synthesis of 2-Hydroxyethyl Methacrylate-Styrene ABA Type Block Copolymers and It's Wettability", Nippon Kagaku Kaishi, 1, 88 to 92).

EXAMPLE 13

There was prepared a solution with the total amount of 9 ml by dissolving 5 ml of the epoxidated gel obtained in Preparation Example 1 in water. After dissolving 0.09 g of L-tyrosine in the solution, the pH value of the mixture was adjusted to pH 9 by adding 2N NaOH, and then the mixture was allowed to stand at room temperature for 2 hours. After the reaction was completed, the gel was filtered off from the reaction mixture and washed with water to give a cellulose gel with immobilized tyrosine.

Measurement of the Concentration of SAP Protein

Each adsorbent obtained in Examples 10 to 13 and CK gel A3 were filled respectively in test tubes made of polypropylene, to which 0.5 ml of human serum including SAP protein. After shaking the mixture at 37° C. for 2 hours, concentration of SAP protein in the supernatant was measured according to ELISA Method. That is, the diluted sample was dropped on a plate coated with an antibody to SAP protein to cause antigen-antibody reaction. Then, peroxidase lavelling anti-SAP protein antibody was added thereto, and the color reaction was observed by using CS-930. The compounds having anionic functional groups immobilized onto the adsorbent and ratio of adsorbing SAP protein of the adsorbent are shown in Table 4. The ratio of adsorbing SAP protein was shown as reducing ratio of the concentration of SAP protein in the supernatant of the adsorbent based on the concentration of SAP protein in the supernatant of CK gel A3.

TABLE 4

| Ex. No. | Compounds having the anionic functional group | Ratio of adsorbing SAP protein (%) |
| --- | --- | --- |
| 10 | Sulfanilic acid | 100 |
| 11 | Sodium dextran sulfate | 77.4 |
| 12 | Polyacrylic acid | 92.5 |
| 13 | L-tyrosine | 58.4 |

From the results shown in Table 4, it is confirmed that the adsorbent of the present invention can adsorb SAP protein excellently.

In addition to the ingredients used in the Examples, other ingredients can be used in the Examples as set forth in the specification to obtain substantially the same results.

What we claim is:

1. A method for removing serum amyloid protein form body fluid comprising the sequential steps of:
   a) combining body fluid containing serum amyloid protein with an adsorbent for the serum amyloid protein comprising a water-insoluble carrier and either
      (i) a group bonded to said carrier of the formula: $-NR^1R^2$, wherein $R^1$ is a hydrogen atom, methyl group or ethyl group, and $R^2$ is an atomic group satisfying the value of log P from 0 to 3.2, in which P is a distribution coefficient in a water-octanol system of a compound of the formula $R^2H$, or
      (ii) a compound immobilized onto said carrier selected from the group consisting of aniline and an aniline derivative;
   b) passing the body fluid containing said adsorbent through a filter through which the adsorbent cannot pass; and
   c) recovering substantially serum amyloid protein free body fluid.

2. A method for removing serum amyloid protein from body fluid comprising the sequential steps of:
   a) combining body fluid containing serum amyloid protein with a adsorbent for the serum amyloid protein comprising a water-insoluble carrier and a compound immobilized onto said carrier selected from the group consisting of aniline and an aniline derivative;
   b) passing the body fluid containing said adsorbent through a filter through which the adsorbent cannot pass; and
   c) recovering substantially serum amyloid protein from body fluid.

3. The method of claim 2, wherein said serum amyloid protein is serum amyloid A protein.

4. The method of claim 2, wherein said serum amyloid protein is serum amyloid P protein.

5. The method of claim 2, wherein said group is bonded to at least part of the surface of said water-insoluble carrier.

6. A method for removing serum amyloid protein from body fluid comprising the sequential steps of:
   a) combining body fluid containing serum amyloid protein with an adsorbent for the serum amyloid protein comprising a water-insoluble carrier and a group, bonded to said carrier, of the formula: $-NR^1R^2$, wherein $R^1$ is a hydrogen atom, methyl group or ethyl group, and $R^2$ is an atomic group satisfying the value of log P from 0–3.2 in which P is a distribution coefficient in a water-octanol system of a compound of the formula $R^2H$;
   b) passing the body fluid containing said adsorbent through a filter through which the adsorbent cannot pass; and
   c) recovering substantially serum amyloid protein free body fluid.

7. The method of claim 6, wherein said serum amyloid is serum amyloid A protein.

8. The method of claim 6, wherein said serum amyloid protein is serum amyloid P protein.

* * * * *